US006843900B2

(12) United States Patent
Dutta et al.

(10) Patent No.: US 6,843,900 B2
(45) Date of Patent: Jan. 18, 2005

(54) POTENTIOMETRIC NOX SENSORS BASED ON YTTRIA-STABILIZED ZIRCONIA WITH ZEOLITE MODIFIED ELECTRODE

(75) Inventors: Prabir K. Dutta, Columbus, OH (US); Nicholas F. Szabo, Columbus, OH (US); Hongbin Du, Ottawa (CA); Sheikh A. Akbar, Hilliard, OH (US)

(73) Assignee: The Ohio State University, Columbus, OH (US)

( * ) Notice: Subject to any disclaimer, the term of this patent is extended or adjusted under 35 U.S.C. 154(b) by 129 days.

(21) Appl. No.: 10/040,036

(22) Filed: Jan. 3, 2002

(65) Prior Publication Data

US 2003/0121780 A1 Jul. 3, 2003

(51) Int. Cl.⁷ ............................................. G01N 27/407
(52) U.S. Cl. ....................... 204/424; 204/426; 204/429; 205/781
(58) Field of Search ................................ 204/421–429; 205/781

(56) References Cited

U.S. PATENT DOCUMENTS

| | | | | |
|---|---|---|---|---|
| 3,752,753 A | * | 8/1973 | Fitterer | |
| 4,193,857 A | * | 3/1980 | Bannister et al. | |
| 4,663,017 A | * | 5/1987 | Ross | |
| 5,413,691 A | * | 5/1995 | Kaneyasu et al. | |
| 5,705,129 A | | 1/1998 | Takahashi et al. | ............ 422/90 |
| 5,897,759 A | * | 4/1999 | Kurosawa et al. | |
| 6,062,064 A | | 5/2000 | Yoshida et al. | ............. 73/23.2 |
| 6,254,749 B1 | * | 7/2001 | Yokota et al. | ............. 204/424 |
| 6,468,407 B2 | * | 10/2002 | Clyde et al. | |
| 6,551,497 B1 | * | 4/2003 | Gao et al. | |

FOREIGN PATENT DOCUMENTS

JP 04359144 * 12/1992

OTHER PUBLICATIONS

N. Miura, G. Lu and N. Yamazoe, *High–temperature potentionmetric/amperometric NOx sensors combining stabilized zirconia with mixed–metal oxide electrode*, Sensors and Actuators B, 52 (1998) 169–178.

N. Miura, H. Kurosawa, M. Hasei, G. Lu and N. Yamazoe, *Stabilized zirconia–based sensor using oxide electrode for detection of NOx in high–temperature combustion–exhausts*, Solid State Ionics, 86–88 (1996) 1069–1073.

N. Miura, G. Lu, N. Yamazoe, H. Kurosawa and M. Hasei, *Mixed Potential Type NOx Sensor Based on Stabilized Zirconia and Oxide Electrode*, J. Electrochem. Soc. 143 (2) (1996) L33–L35.

G. Lu, N. Miura and N. Yamazoe, *Stabilized zirconia–based sensors using WO3 electrode for detection of NO or NO2*, Sensors and Actuators B, 65 (2000) 125–127.

H. Kurosawa, Y. Yan, N. Miura and N. Yamazoe, *Stabilized zirconia–based NOx sensor operative at high temperature*, Solid State Ionics, 79 (1995) 338–343.

E.L. Brosha, R. Mukundan, D.R. Brown, F.H. Garzon, J.H. Visser, M.Zanini, Z. Zhou and E.M. Logothetis, *CO/HC sensors based on thin films of LaCoO3 and La0.8Sr0.2CoO3–δ metal oxides*, Sensors and Actuators B, 69 (2000) 171–182.

(List continued on next page.)

Primary Examiner—Kaj K. Olsen
(74) Attorney, Agent, or Firm—Standley Law Group LLP

(57) ABSTRACT

A potentiometric sensor for nitrogen oxide ($NO_x$) measurement based on yttria-stabilized zirconia with a zeolite-modified electrode is presented. A potentiometric sensor of the present invention comprises a tube having an interior and an exterior. A cap member comprising yttria-stabilized zirconia closes one end of the tube. The cap member has an interior surface exposed to the interior of the tube where a first electrode is disposed. The first electrode is then covered with a zeolite layer. A second electrode is disposed on the exterior of the cap member.

22 Claims, 19 Drawing Sheets

OTHER PUBLICATIONS

R. Mukundan, E.L. Brosha, D.R. Brown and F.H. Garzon, *Ceria–Electrolyte–Based Mixed Potential Sensors for the Detection of Hydrocarbons and Carbon Monoxide, Electrochemical and Solid State Letters*, 2(8) (1999) 412–414.

R. Mukundan, E.L. Brosha, D.R. Brown and F.H. Garzon, *A Mixed–Potential Sensor Based on a Ce0.8Gd0.2O1.9 Electrolyte and Platinum and Gold Electrodes, J. Electrochem. Soc.* 147 (4) (2000) 1583–1588.

T. Hibino, S. Kakimoto and M. Sano, *Non–Nernstian Behavior at Modified Au Electrodes for Hydrocarbon Gas Sensing, J. Electrochem. Soc.* 146 (9) (1999) 3361–3366.

A. Walcarius, *Zeolite–Modified Electrodes in Electroanalytical Chemistry, Analytical Chimica Acta*, 384, pp. 1–16 (1999).

A. Walcarius, *Factors Affecting the Analytical Applications of Zeolite Modified Electrodes: Indirect Detection of Non-electroactive Cations, Analytical Chimica Acta*, 388, pp. 79–91 (1999).

K. Fukui, S .Nishida, *CO Gas Sensor Based on Au–La$_2$O$_3$ Added SnO$_2$ Ceramics with Siliceous Zeolite Coat, Sensors and Actuators B*, 45, pp. 101–106 (1997).

H.Tsuchiya, I. Sasaki, A. Harano, T. Okubo and M. Sadakata, *Zeolite Sensor for Nitrogen Monoxide Detection at High Temperature, Mat. Res. Soc. Symp. Proc.*, 454, pp. 297–302 (1997).

O. Enea, *Morphological and Electrocatalytic Properties of Gold Deposits on NaY Zeolite, Electrochim. Acta.*, pp. 1647 34 (1989).

M. Osada, I. Sasaki, M. Nishioka, M. Sadakata, T. Okubo, *Synthesis of a Faujasite Thin Layer and its Application for SO$_2$ Sensing at Elevated Temperatures, Microporous and Mesoporous Materials*, 23, pp. 287–294 (1998).

B. Liu, F. Yang, J. Kong, J. Deng, *A Reagentless Amperometric Biosensor Based on the Coimmobilization of Horseradish Peroidase and Methylene Green in a Modified Zeolite Matrix, Analytica Chimica Acta*, 386, pp. 31–39 (1999).

U. Kunzellman, H. Bottche, *Biosensor Properties of Glucose Oxidase Immobilized Within SiO$_2$ Gels, Sensors and Actuators B*, 39, pp. 222–228 (1997).

U. Simon, U. Flesch, W. Maunz, R. Muller, C. Plog, *The effect of NH$_3$ on the Ionic Conductivity of Dehydrated Zeolites Nabeta and Hbeta, Microporous and Mesoporous Materials*, 21, pp. 111–116 (1998).

O.S. Wolfbeis, *Novel Oxygen Sensor Material Based on a Ruthenium Bipyridyl Complex Encapsulated in Zeolite Y: Dramatic Differences in the Efficiency of Luminescence Quenching by Oxygen on Going From Surface–Absorbed to Zeolite–Encapsulated Flourophores, Sensors and Actuators B*, 29, pp. 240–245 (1995).

R. Berger, Ch. Gerber, H.P. Lang, J.K. Gimzewski, *Micromechanic: A Toolbox for Femtoscale Science: Towards a Laboratory on a Tip, Microelectronic Engineering*, 35, pp. 373–379 (1997).

L. Scandella, G. Binder, T. Mezzacasa, J. Gobrecht, R. Berger, H.P. Lang, Ch. Gerber, J.K. Gimzewski, J.H. Koegler, J.C. Jansen, *Combination of Single Crystal Zeolites and Microfabrication: Two Applications Toward Zeolite Nanodevices, Microporous and Mesoporous Materials*, 21, pp. 403–409 (1998).

* cited by examiner

30

40

POTENTIOMETRIC NOX SENSORS BASED ON YTTRIA-STABILIZED ZIRCONIA WITH ZEOLITE MODIFIED ELECTRODE

The present invention was made with Government support under Grant No. EEC-9523358 awarded by the National Science Foundation. The United States Government may have certain rights to this invention under 35 U.S.C. §200 et seq.

TECHNICAL FIELD OF INVENTION

The present invention relates to nitrogen oxide ($NO_X$) measurement systems for use in harsh environments. The present invention provides sensors based on the solid electrolyte yttria stabilized zirconia (YSZ) with platinum (Pt) electrodes where one electrode is modified by a zeolite NaY coating.

BACKGROUND OF THE INVENTION

Due to a continuing need for the development of rugged and reliable sensors capable of taking measurements in harsh industrial environments, there has been extensive research in this area as evidenced by the technical literature.

For example, Yamazoe et al. has reported a series of sensors based on stabilized zirconia with mixed metal oxide electrode systems. A $CdCr_2O_4$ attached device was reported as a good potentiometric sensor for $NO_X$ gases in the temperature range of 500 to 600° C. In several other papers, they have studied different metal oxide systems and found $CdMn_2O_4$ as a good candidate for sensing applications. They have also proposed a $NO_X$ sensing mechanism involving mixed potential based on the measurements of polarization curves.

Lu et al. has recently reported the study of YSZ (yttria stabilized zirconia) based sensors using a tungsten tri-oxide ($WO_3$) electrode for the detection of NO and $NO_2$. The EMF response of the $WO_3$-attached device is nearly linear to the logarithm of NO or $NO_2$ concentrations. Kurosawa et al. has fabricated a $NO_X$ sensor based on MgO stabilized zirconia with an auxiliary phase of $Ba(NO_3)_2$. E. L. Brosha et al. has reported mixed potential sensors based on dense, thin films of lanthanum cobaltate pervoskites for carbon monoxide (CO) and hydrocarbon gases. R. Mukundan et al. has studied mixed potential YSZ and $CeGdO_X$ based sensors with platinum (Pt) and gold (Au) electrodes for hydrocarbon and CO sensing measurements. According to them, a $CeGdO_X$ based sensor gave a more stable and reproducible response than a YSZ electrolyte due to the better oxygen reduction kinetics of metal electrodes on ceria-based electrolytes. The same group has reported that the reproducibility of the response behavior was dependent of Au morphology. T. Hibino et al. has reported non-Nernstian behavior at tantalum oxide modified Au electrodes for hydrocarbon sensing.

Zeolites have recently become the subject of considerable research in sensor applications. In the past 15 years there has been considerable research done on zeolite modified electrodes (ZMEs), the study of putting a layer containing zeolite particles onto an electrode surface. Walcarius classifies five main applications of ZMEs, which include electrocatalysis, electroanalysis, charge storage devices, molecular recognition, and mass transport characterization. For utilization in sensor materials, electroanalysis is of particular importance. Walcarius sub-divides this application into the five categories of direct detection, indirect detection, amperometric biosensors, potentiometric analysis, and voltametry after preconcentration. Various methods have been used to cover the electrode such as zeolite dispersion in a binder, pressing zeolite powder onto the electrode, applying a coating of the zeolite in a polymer matrix, and covalently linking zeolite to the surface of the electrode. The majority of electroanalysis applications using ZMEs have been for determination of species, usually metal cations, in the liquid phase.

There have been few accounts of using zeolite materials for gas phase sensing at various temperatures and conditions. One design studied is a sensor operating at 300° C. for the detection of CO using $SnO_2$ coated onto a platinum wire. The $SnO_2$ is impregnated with Au—$La_2O_3$ and this layer is subsequently covered with a layer of the zeolite ferrierite. The addition of the zeolite serves as a catalyst filter to allow selectivity for CO in the presence of $H_2$, $CH_4$, $C_2H_4$, i-$C_4H_{10}$ and $C_2H_5OH$.

Au—NaY zeolite electrodes are used to monitor ethanol and ammonia vapors using cyclic voltametry. High current densities are obtained in the presence of ethanol and ammonia vapors at 25° C.

Zeolites deposited on a quartz crystal microbalance (QCM) are used as sensors for gaseous molecules. Cu-ZSM-5 zeolite is deposited onto a quartz substrate with a gold (Au) electrode and used to detect NO in helium (He) at 384K. The shift of the fundamental resonance frequency of the QCM was found to be proportional to the amount of NO present. A similar study done at 423K involving a thin layer of the zeolite faujasite on a QCM with Au electrodes detected $SO_2$ in the presence of $O_2$. Other studies involving sensor based systems include: the use of zeolites in amperometric biosensors for $H_2O_2$ and glucose oxidase, $NH_3$ detection by monitoring the change of conductivity of zeolite $Na^+$ beta and $H^+$ beta measured by impedance spectroscopy, use of the zeolite NaY—($Ru^{2+}(bpy)_3$) as a fluorescence $O_2$ sensor, and for gas detection by micromechanical cantilevers attached with zeolite crystals at the apex.

There is a continuing need for the development of rugged and reliable sensors capable of making measurements in the harsh industrial environments found in the steel, heat treating, metal casting, glass, ceramic, pulp and paper, automotive, aerospace, and utility and power industries. The 1990 Clean Air Act amendments (CAAA) will require many power and utility industries to monitor emissions. Emission monitoring sensors for these applications include those for CO, $NO_X$, $O_2$ and hydrocarbons. Combustion engines are a major contributor of $NO_X$ emissions. The major species of $NO_X$ in automotive exhaust gases are NO, $NO_2$ and $N_2O$ of which 90% of the total amount is NO. Nitrogen oxides can be toxic to humans, with possible lung impairment due to exposure of less than 15 ppm $NO_2$. It is therefore imperative to develop a sensor for $NO_X$ that will provide real time analysis for engine control and onboard diagnostics to monitor and control these emissions.

SUMMARY OF THE INVENTION

The present invention presents a novel potentiometric sensor.

A potentiometric sensor of the present invention comprises an alumina tube having an interior and an exterior. A cap member closes one end of the tube. The cap member has an interior surface exposed to the interior of the alumina tube and an exterior surface. The cap member comprises yttria-stabilized zirconia. A first electrode is disposed on the interior surface of the cap member. The first electrode is covered by zeolite. The zeolite is in the interior of the alumina tube. A second electrode is disposed on the exterior surface of the cap member.

It is preferred that a potentiometric sensor of the present invention additionally comprise a measurement apparatus (potentiometer) that measures the electrical potential between the first and second electrodes disposed on the sensor. Further, it is preferred that the first electrode, second electrode or both electrodes comprise a material selected from the group consisting of platinum, gold and $Cr_2O_3$. Additionally, it is preferred that the zeolite is Zeolite Y.

A second embodiment of a sensor of the present invention is a potentiometric sensor comprising a tube having an exterior and an interior. The tube comprises yttria-stabilized zirconia. A first electrode is disposed of the exterior of the tube and a second electrode is disposed on the interior of the tube. A zeolite material covers one of the electrodes.

It is preferred that a potentiometric sensor of the present invention additionally comprise a measurement apparatus (potentiometer) that measures the electrical potential between the first and second electrodes disposed on the tube. Further, it is preferred that the first electrode, second electrode or both electrodes comprise a material selected from the group consisting of platinum, gold and $Cr_2O_3$. Additionally, it is preferred that the zeolite is Zeolite Y.

A third embodiment of a sensor of the present invention is a potentiometric sensor comprising a substrate. The substrate comprises yttria-stabilized zirconia. A first electrode is disposed on the substrate. A second electrode is disposed on the substrate and covered with a layer of zeolite. The electrodes may be disposed on the same side of the substrate or may be placed on opposite surfaces of the substrate.

It is preferred that a potentiometric sensor of the present invention additionally comprise a source of an electrical potential supplied to the electrodes and a potentiometer in electrical contact with the source of electrical potential. Further, it is preferred that the first electrode, the second electrode or both electrodes comprise a material selected from the group consisting of platinum, gold and $Cr_2O_3$. Additionally, it is preferred that the zeolite is Zeolite Y.

In a most preferred Type 3 sensor embodiment of the present invention, a porous member may shield the substrate and the first and second electrodes from the harsh exhaust gas environment. The porous member prevents the exhaust gas from directly contacting the substrate and the first and second electrodes. The exhaust gas can come in contact with these elements only after traveling through the porous member. In this way, the porous member prevents degradation of the sensitive underlying elements such as the substrate, first electrode and second electrode.

BRIEF DESCRIPTION OF THE DRAWINGS

Novel features and advantages of the present invention, in addition to those mentioned above, will become apparent to those skilled in the art from a reading of the following detailed description in conjunction with the accompanying drawings wherein similar reference characters refer to similar parts and in which.

DETAILED DESCRIPTION OF THE PREFERRED EMBODIMENT(S)

Figure 1:
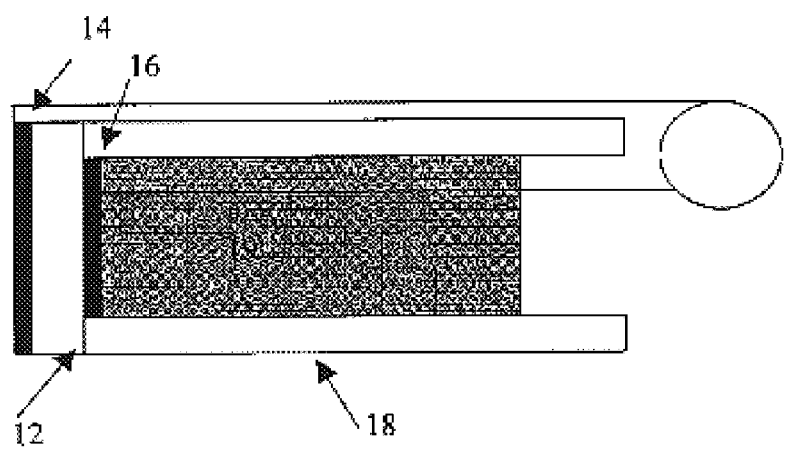
FIG. 1 shows a sensor (Type 1) of the present invention.

Three sensor designs based upon the same principle are disclosed. The first sensor 10 (Type 1), shown in FIG. 1, is comprised of a YSZ pressed pellet 12 with a first platinum (Pt) electrode 14 and a second platinum electrode 16 mounted onto an alumina tube 18 packed with zeolite NaY (LZY-52 from Union Carbide) 19. The YSZ pellet was constructed from commercially available YSZ powder (HSY-8, Zirconia Sales Inc., 8 mol % YSZ). The pellet was formed in a stainless steel die (Carver Inc.) under 10,000 psi on a Carver pellet press. The green pellet was put onto an alumina plate and sintered in a Lindberg Blue high temperature box furnace at 1450° C. for 6 hours with 6° C./min heating and cooling rates. The final pellet dimensions were approximately 9 mm in diameter and 2 mm thick. The pellet was white in color. Pt ink (Englehard Corporation, lot #A47331) was painted on both sides of the pellet and Pt lead wires (Englehard Corporation, 31 AWG) were set into the wet Pt ink. The ink was then cured in a Lindberg Blue box furnace at 1250° C. for 2 hours with a heating and cooling rate of 6° C./min. The resulting electrodes had a metallic grey color. The pellet was then mounted onto an alumina tube (Coors Ceramic), approximately 1 inch in length, with a high temperature inorganic adhesive, Ceramabond 569 (Aremco). Thus, one lead wire was on the outside of the tube and the other wire on the inside. The Ceramabond was then left to dry for 1–2 hours at room temperature. The purpose of the tube is to hold zeolite powder, which was then packed on the inside as to cover the electrode. After final assembly, the sensor was put into a tube furnace at 500° C. for a few hours to thermally stabilize it before testing.

Figure 2:
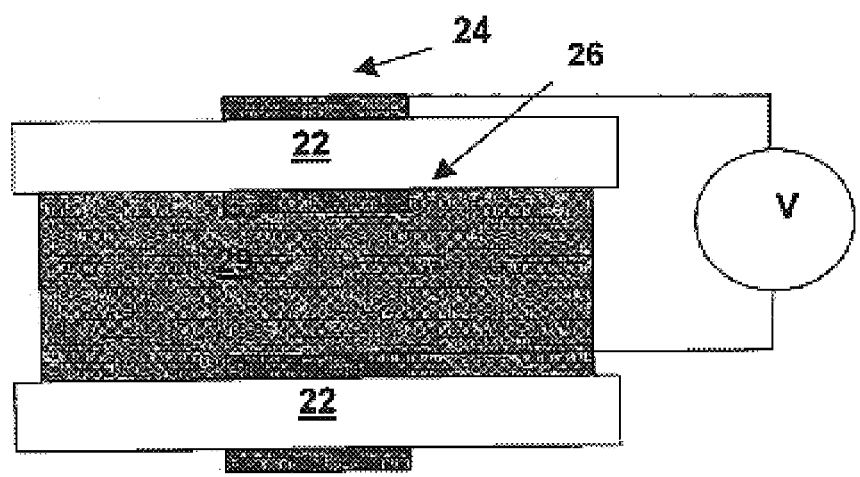
FIG. 2 shows a sensor (Type 2) of the present invention.

The second sensor 20 (Type 2), shown in FIG. 2, comprises a cylindrical piece of 8 mol % YSZ 22 (Vesuvius McDanel), approximately 20 mm length, 6 mm outside diameter, 4.5 mm inside diameter, cut with a diamond saw (Leco). Pt electrodes 24 and 26 were prepared in a similar manner as the type 1 design. After the sensor body was prepared, zeolite NaY powder 29 was packed into the inside as to cover the inside electrode 26. The final sensor was then heated at 500° C. in a tube furnace to achieve thermal equilibrium before testing.

Figure 3:
FIG. 3 shows a sensor (Type 3) of the present invention.
Figure 3:
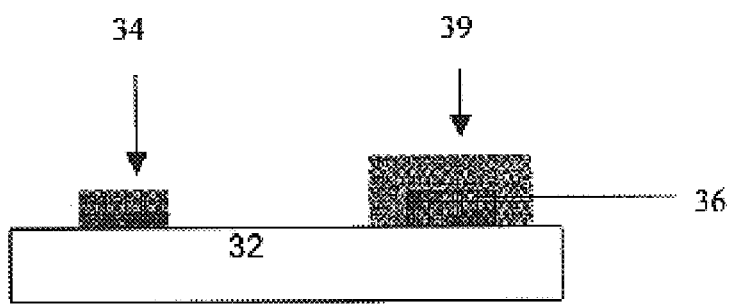

The third sensor 30 (Type 3), shown in FIG. 3, comprises a YSZ pellet 32 with two Pt electrodes 34 and 36 on the same side (planar structure) with one of the Pt electrodes coated by a layer of zeolite 39. The YSZ pellet and electrodes were prepared using the same materials and methods as the Type 1 design. A viscous zeolite paste was prepared by mixing zeolite NaY powder with terpineol solvent. The paste was applied with a paint brush over one of the Pt electrodes. After the paste application, the sensor was heated in a tube furnace at 500° C. for 2 hours to evaporate the terpineol solvent and stabilize the coating.

Figure 4:
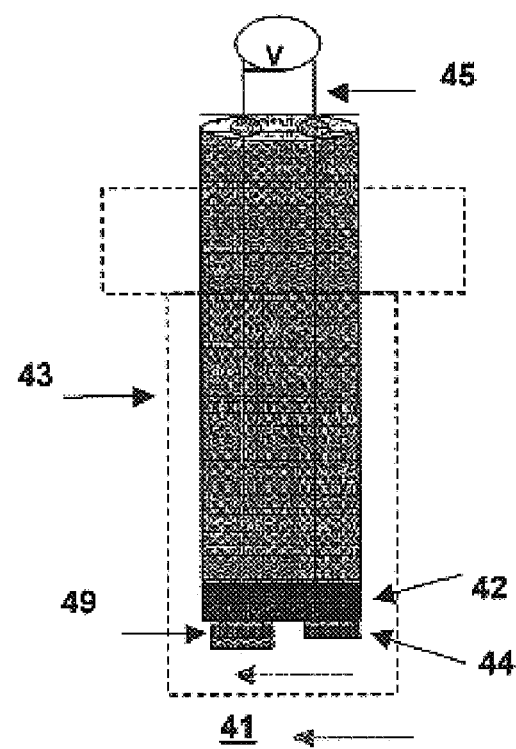
FIG. 4 shows a schematic of an exhaust sensor (Type 3) assembly of the present invention.
Figure 5:
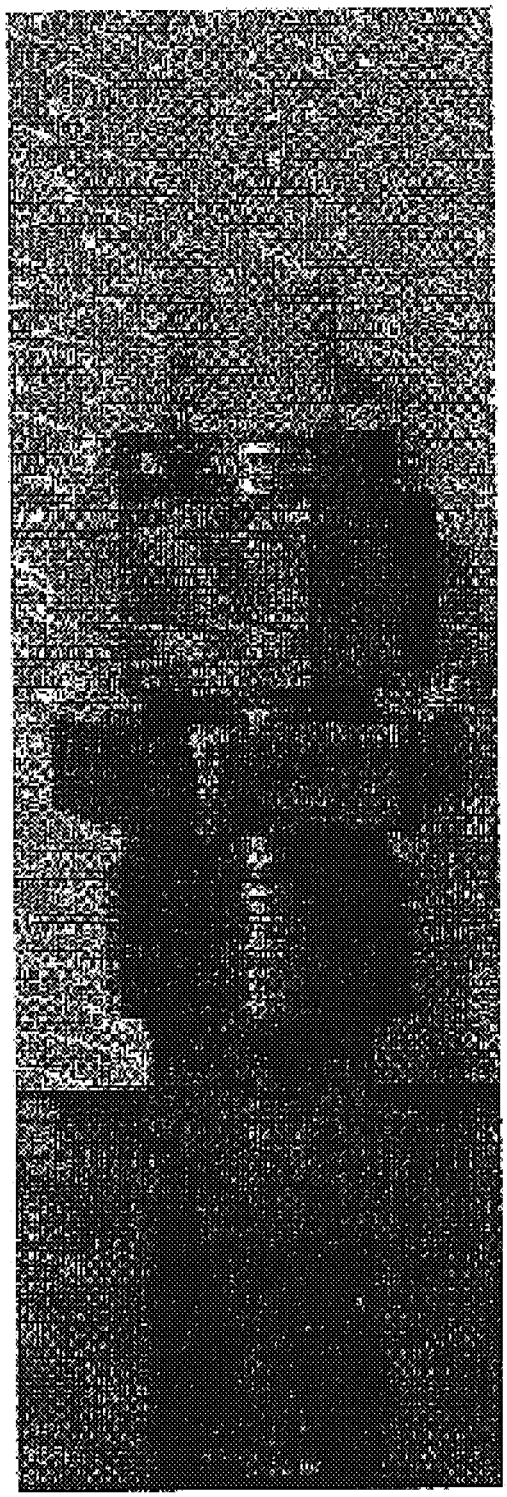
FIG. 5 is a picture of an exhaust sensor assembly of the present invention.

The interest in NO sensors arises because of their possible utility in sensing gases in high temperature combustion processes. Of particular interest to the community is sensing NO emissions from automotive engines. Because of the high temperatures and the presence of high flow rates and particulates in the exhaust, the sensor needs appropriate packaging. The planar sensor (Type 3) lends itself to a possible packaging design that can survive harsh environments. FIG. 4 shows a schematic of how the planar sensor (Type 3) has been incorporated into a spark plug tube. The assembly 40 is subjected to an exhaust gas stream 41. The exhaust gas stream 41 flows over the exposed porous cap 43. The porous cap 43 protects the electrodes 44, 49 from the harsh environment of the exhaust gas stream 41 while permitting the exhaust gas to contact the electrodes. Any suitable material may be used for the porous cap 43 provided that it allows the exhaust gas to contact the electrodes and also protects the electrodes from degradation caused by the harsh exhaust gas environment. The electrodes are each disposed on a YSZ substrate 42. Lead wires 45 connect the electrodes to a potentiometer. FIG. 5 shows an actual picture of the sensor assembly. To improve the mechanical stability of the zeolite layer in a high flow environment a zeolite pellet was placed on top of the zeolite powder and bonded to the YSZ pellet around the edges with Ceramabond.

Figure 6:
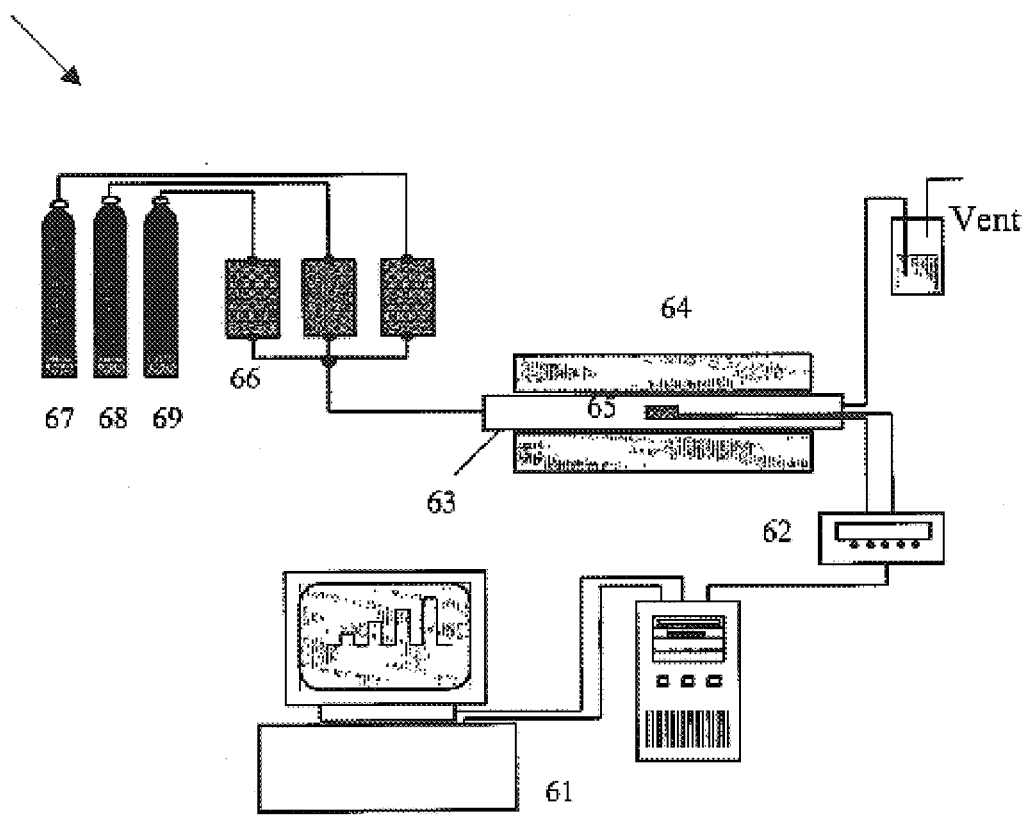
FIG. 6 is a diagram of an experimental testing apparatus.

Gas sensing experiments were performed within a quartz tube located inside a high temperature tube furnace (Lindberg Blue model) shown in FIG. 6. The sensor rested in a quartz tube while the two sensor wires were connected to two Pt wires threaded into the quartz tube, which led outside the furnace. The tube furnace 64 was used to heat and cool the sensor 65 at a programmed rate as well as maintaining it at a temperature between 500–700° C., depending upon the experiment. Air 68, $N_2$ 67 and combustion gases 69 such as NO (2000 ppm source tank), $NO_2$ (1000 ppm source tank) and CO (2000 ppm source tank) were metered through Sierra brand mass flowmeters 66 to form gas mixtures of various compositions, with a volumetric flow rate of 100 cc/min. The voltage output of the sensor response to changes in the gas concentrations were monitored by a Hewlett Packard multimeter 62 (34401A) and recorded by Hewlett Packard Benchlink software on a Windows 95 Pentium based PC 61.

The three sensor types and the automotive exhaust probe were tested and the results are outlined below.

Figure 7:
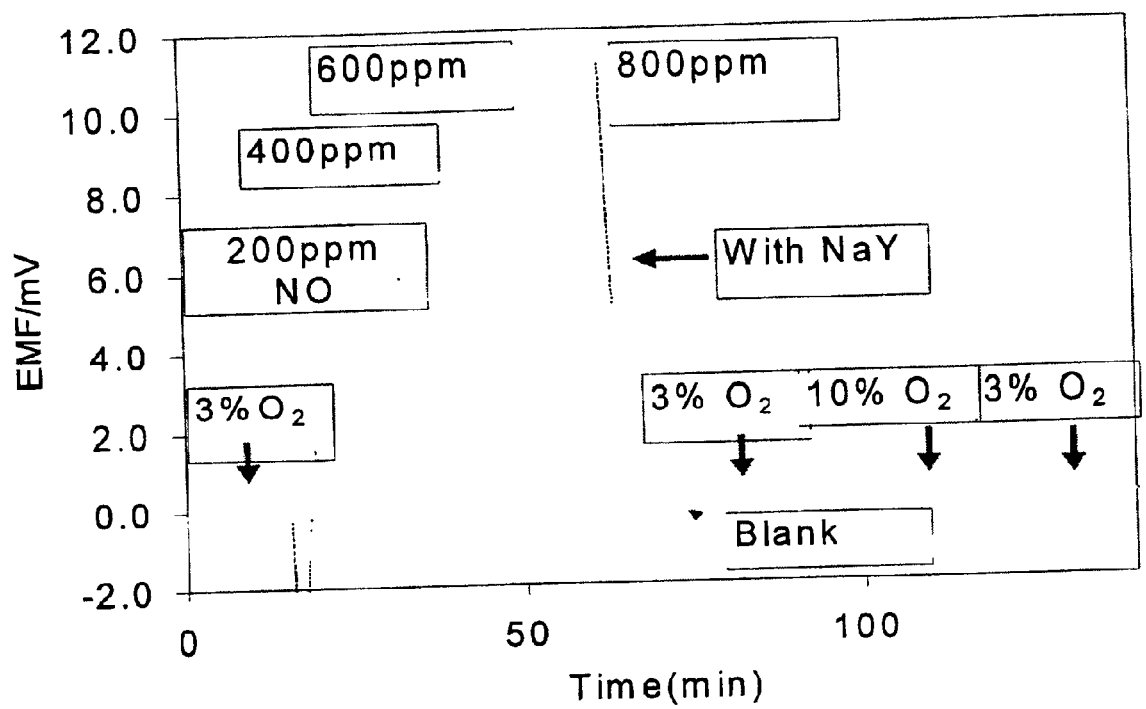
FIG. 7 compares the response of an uncoated Type 3 sensor with a NaY coated Type 3 sensor for 0–800 ppm NO in 3% $O_2$.
Figure 8:
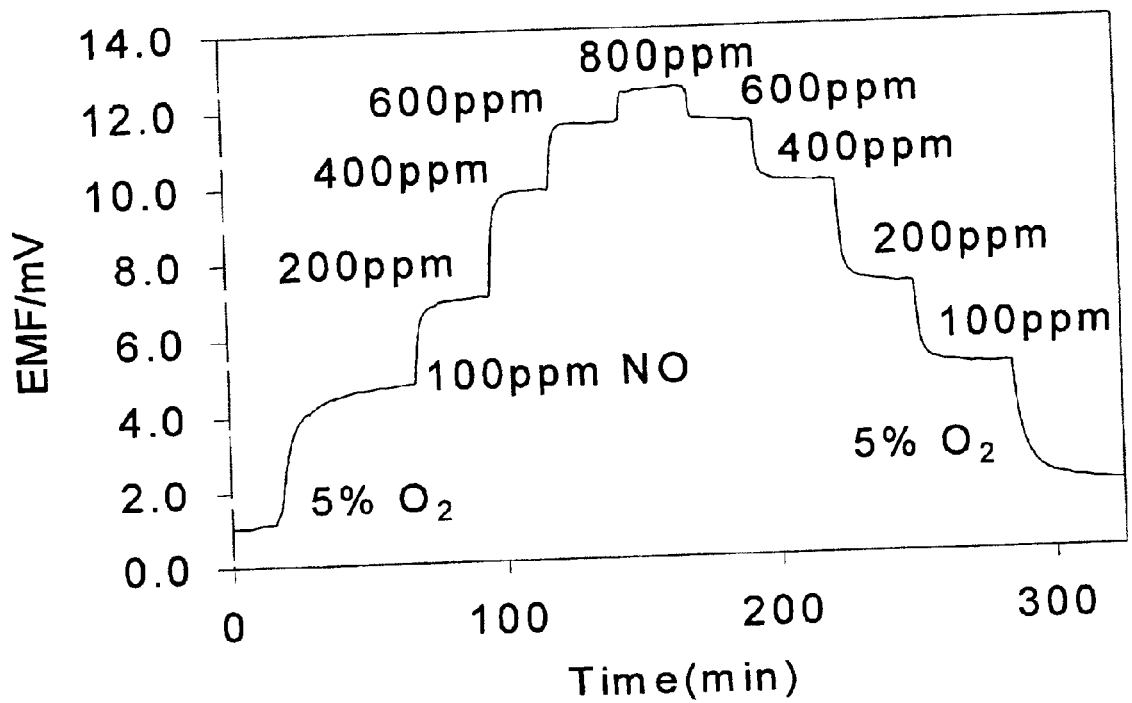
FIG. 8 illustrates a typical Type I sensor output to NO concentration.
Figure 9:
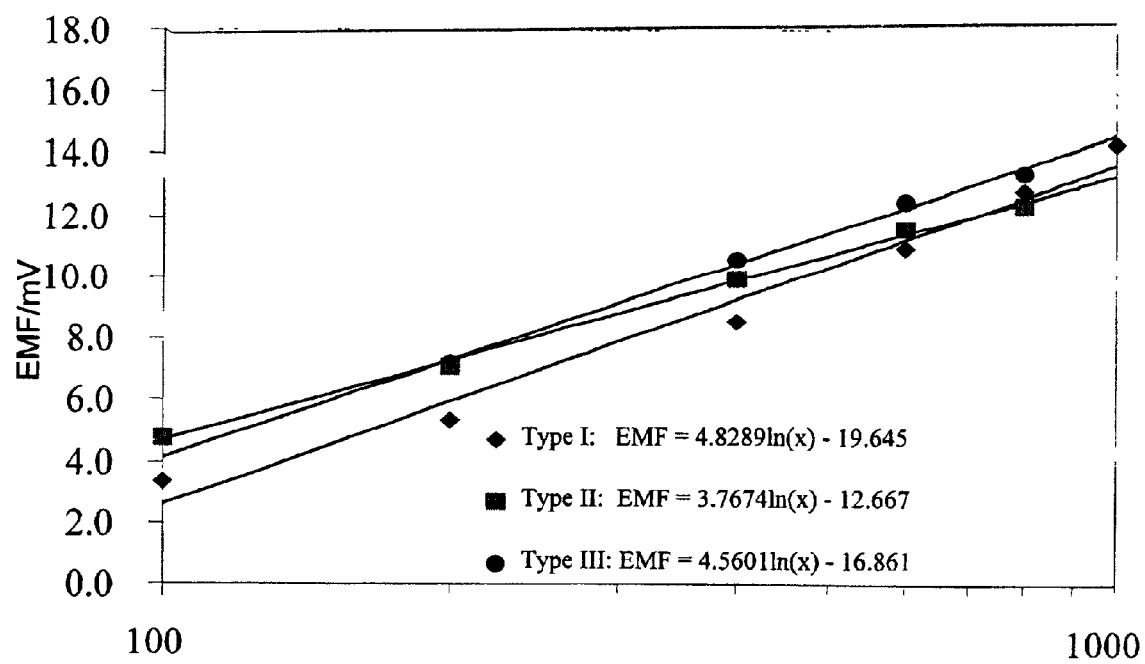
FIG. 9 is a graph showing sensitivity plots for the three types of sensors of the present invention.
Figure 10:
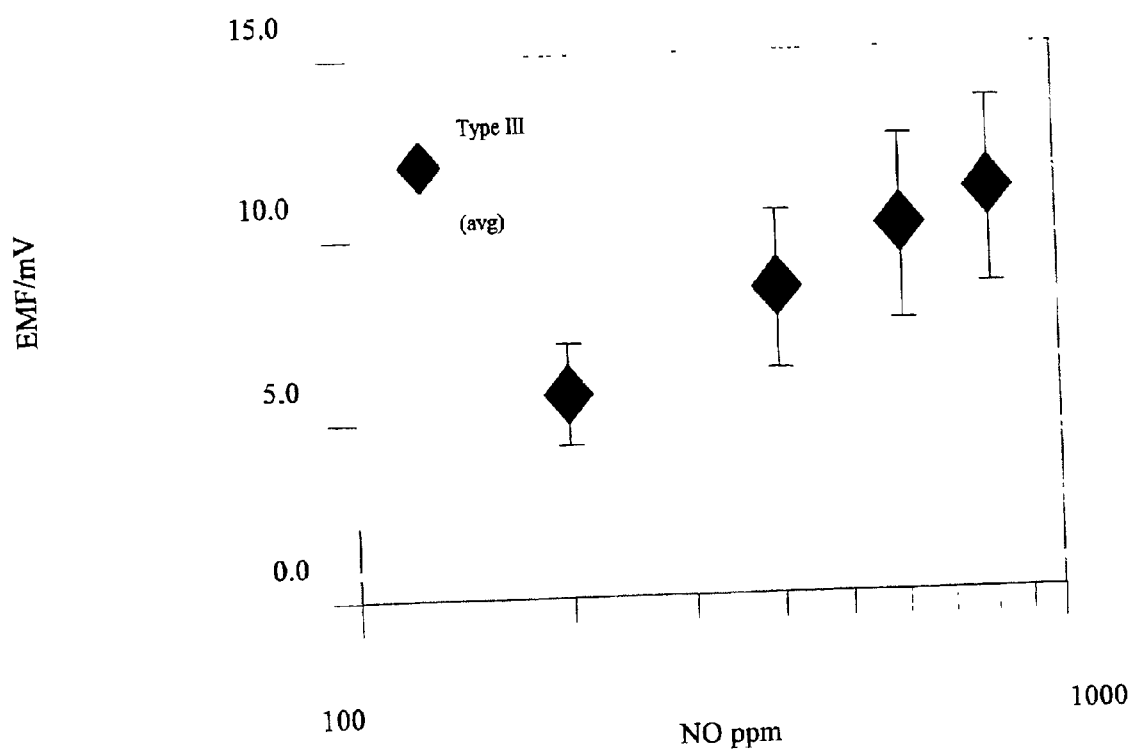
FIG. 10 shows the reproducibility of Type III sensor performance.

FIGS. 1, 2 and 3 show the sensor designs that were investigated. In developing these designs, the strategy is to build asymmetry between the two Pt electrodes by covering one of the electrodes with zeolite NaY. FIG. 7 compares the response of an uncoated (no NaY coating) Type 3 sensor and a NaY coated Type 3 sensor for 0–800 ppm NO in 3% $O_2$. It is evident that the presence of NaY causes an enhanced signal toward NO. All three types of sensors showed similar behavior towards NO, as demonstrated in FIG. 8 for a tubular (Type 1) design. Because of the asymmetry provided by the zeolite layer, it becomes possible to expose the complete sensor to the sensing gases without the need for an air reference. FIG. 9 compares the sensitivity plots for the three designs. The voltage follows a linear dependence with the logarithm of the NO concentration. The reproducibility of sensor performance is for data obtained from three planar sensors where the signal variation for one standard deviation is shown in FIG. 10. The variations are likely due to factors in the fabrication process, including the size and thickness of the Pt electrodes, and the zeolite film thickness and packing.

Next, interference effects will be explored.

Figure 11:
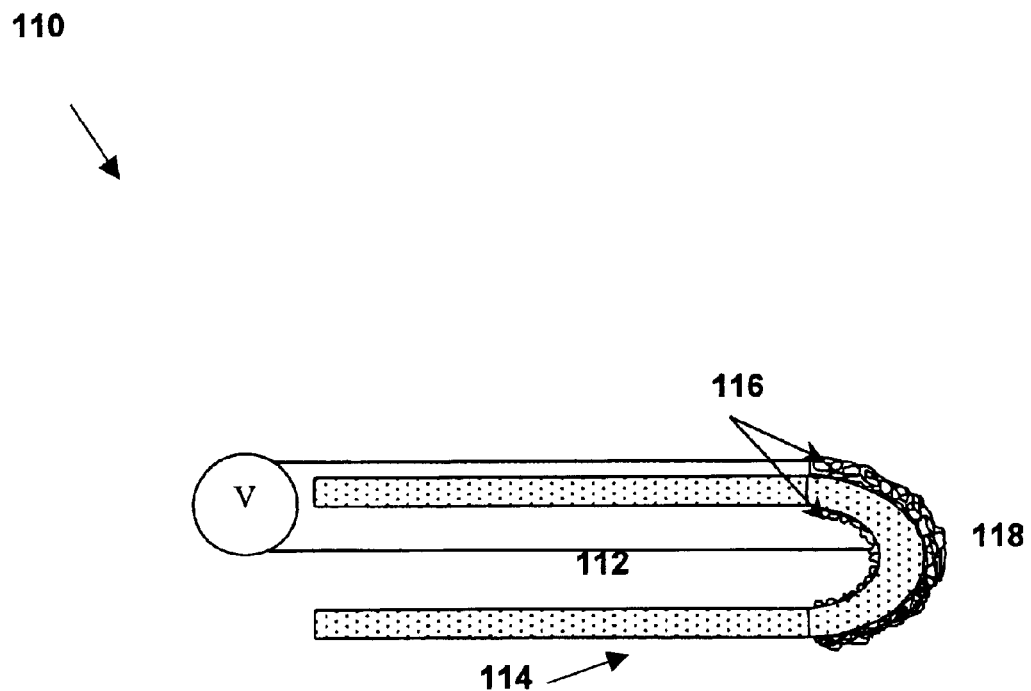
FIG. 11 depicts a YSZ closed-end tube type sensor with an air reference.
Figure 12:
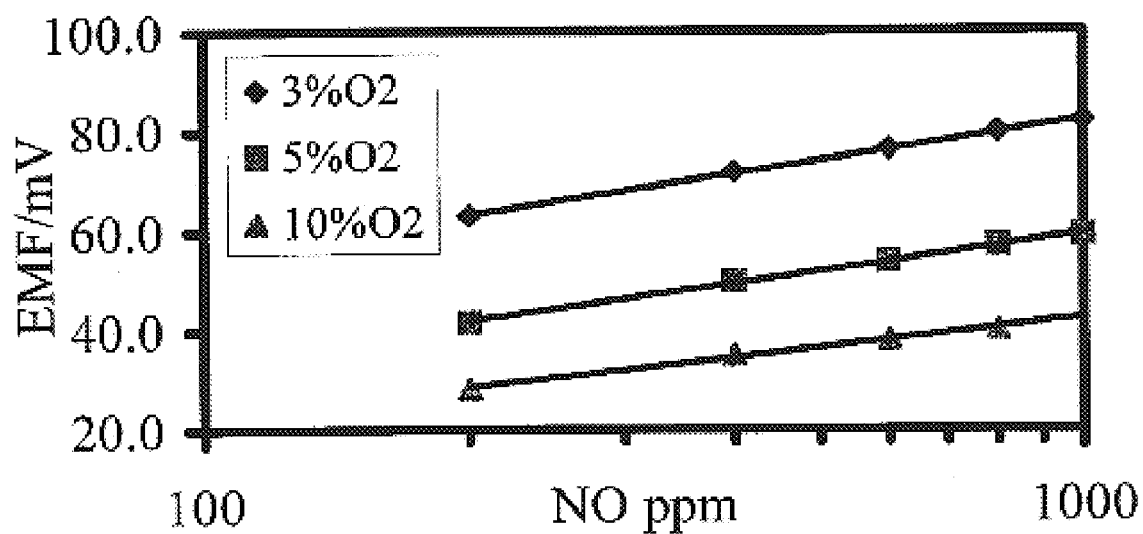
FIG. 12 is a graph of the NO calibration curves for the sensor shown in FIG. 11.
Figure 13:
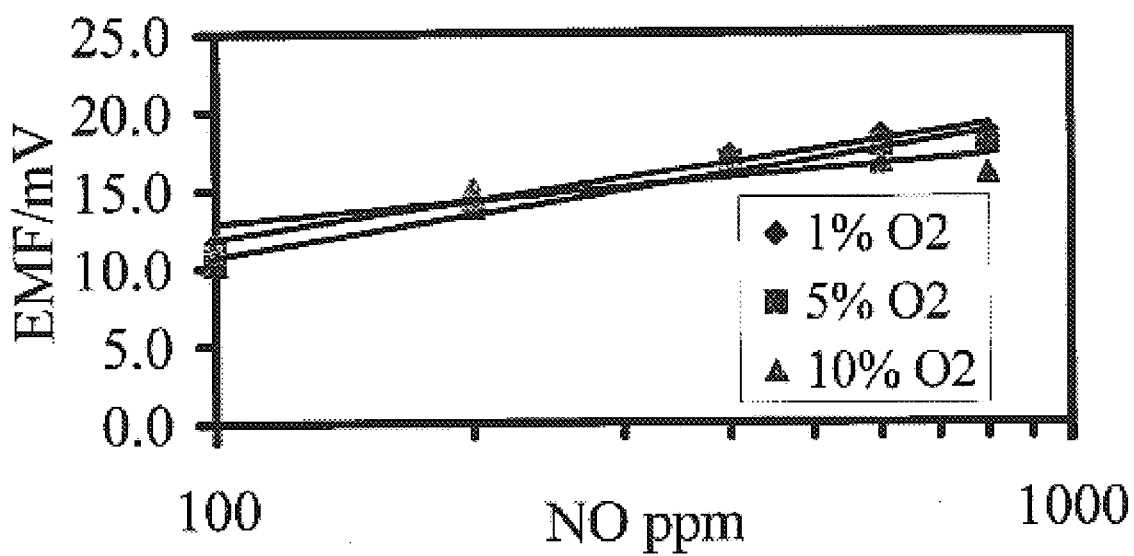
FIG. 13 illustrates the NO calibration curve for a zeolite-based Type 2 sensor.

Since YSZ is an oxygen ion conductor, any imbalance of $O_2$ on two Pt electrodes will alter the baseline. This is demonstrated by using a YSZ closed-end tube type sensor 110 (see FIG. 11) having two Pt electrodes 116 with an air reference 112 where the oxygen inside the YSZ tube 114 is at 21%, whereas the outside of the sensor is exposed to NO 118 (100–1000 ppm) at varying oxygen levels similar to a combustion environment. FIG. 12 shows the NO calibration curves for this sensor. If a similar experiment is done with a zeolite-based sensor (e.g., a Type 2 as shown in FIG. 2), the calibration curve collapse to approximately the same line (FIG. 13), demonstrating that the level of $O_2$ at both Pt electrodes is similar, primarily because the microporosity of the zeolite allows for $O_2$ transport to the underlying Pt electrode. Another manifestation of the same effect can be seen in FIG. 7 with the planar sensor (Type 3) where changing $O_2$ levels does not alter the background signal.

Figure 14:
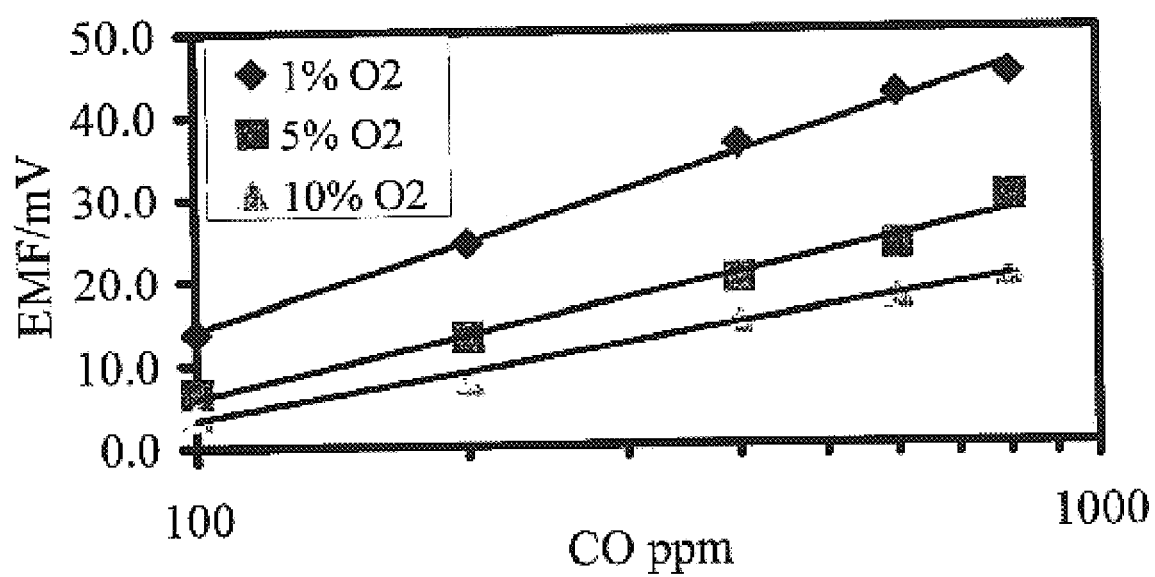
FIG. 14 shows the calibration curves obtained with CO using a Type 2 sensor when exposed to different $O_2$ concentrations.
Figure 15:
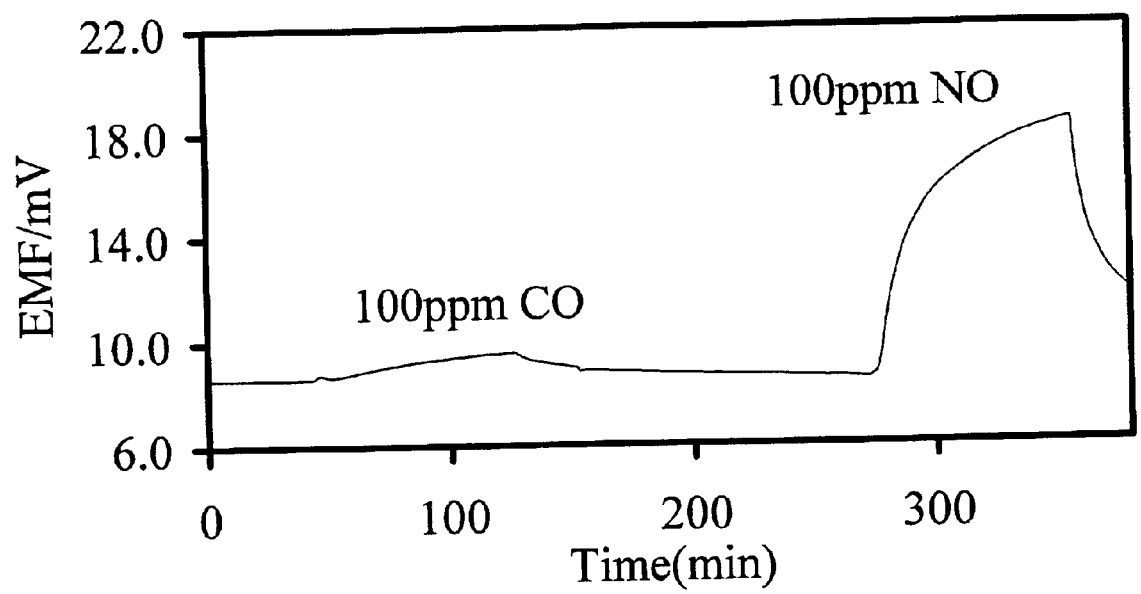
FIG. 15 illustrates the sensor response to both CO and NO in 21% $O_2$.

FIG. 14 shows the calibration curves obtained with CO using sensor type 2 and its dependence on the $O_2$ concentration of the background gas. There is a strong signal from CO due to the electrochemical reaction $CO+O^{2-} \rightarrow CO_2+2e^-$. However, the slope of the calibration curve, which is a measure of sensitivity, decreases with increasing $O_2$ concentration. FIG. 15 shows the sensor trace to both CO and NO in 21% $O_2$, where the sensor appears to be almost insensitive to CO. The gradual decrease in CO signal with $O_2$ is because the CO gets oxidized on the Pt surface at the higher background $O_2$ levels, before it can reach the Pt-YSZ interface for the electrochemical reaction and the oxidation product $CO_2$ is electrochemically inactive.

Figure 16:
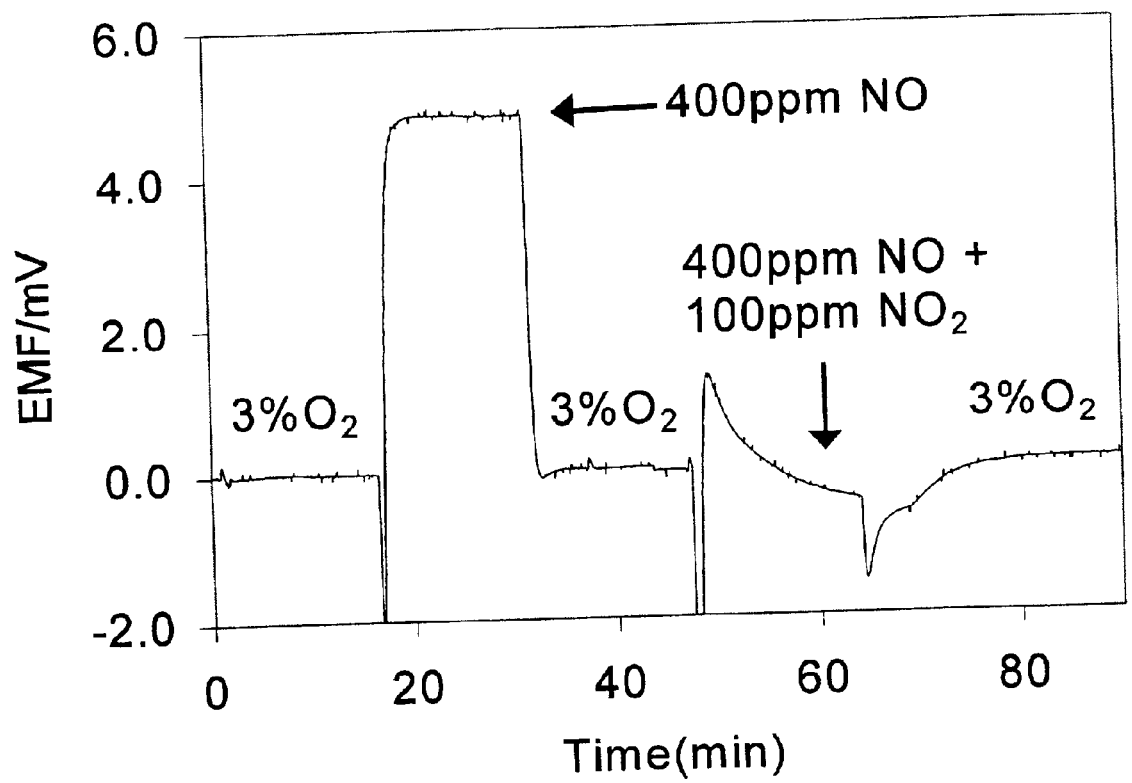
FIG. 16 compares the potentiometric response of a Type 3 sensor to 400 ppm NO and 400 ppm NO+100 ppm $NO_2$ in 3% $O_2$ at 500° C.
Figure 17:
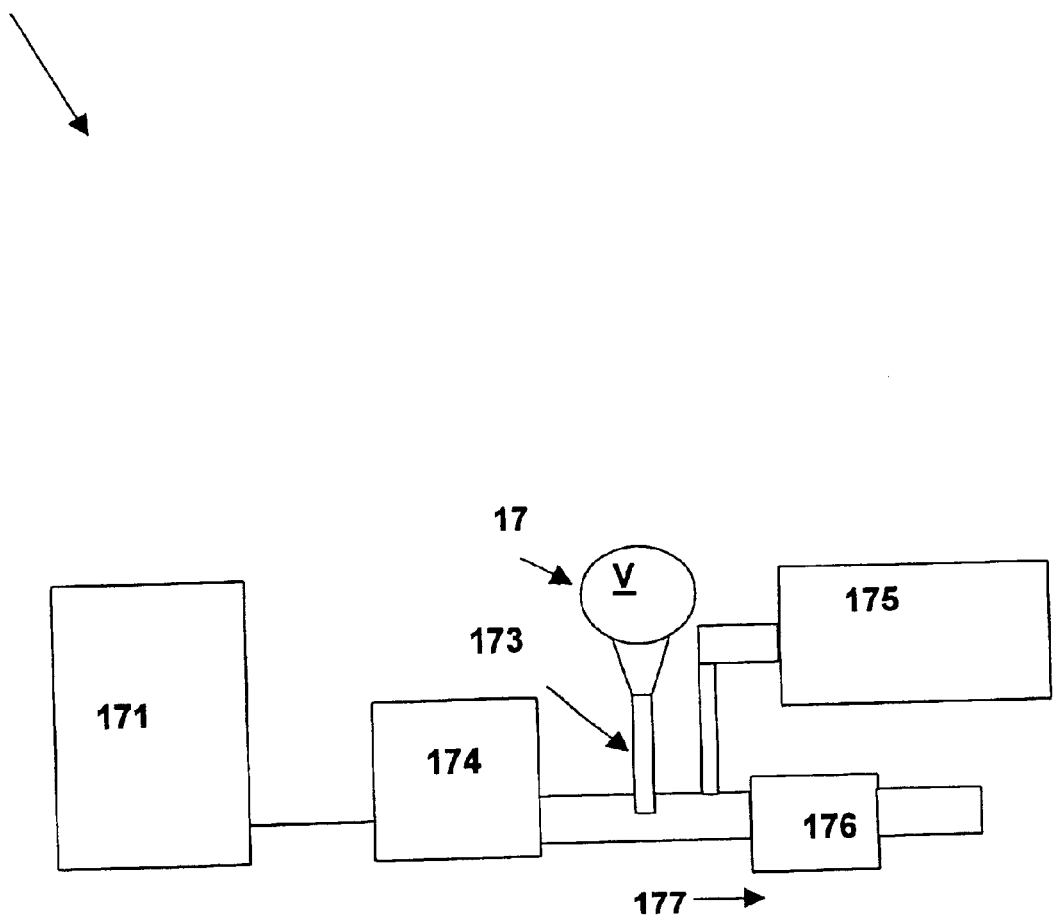
FIG. 17 shows the experimental apparatus used to test the automotive sensor probe shown in FIGS. 4 and 5.

FIG. 16 compares the potentiometric response of a planar sensor (Type 3) to 400 ppm NO and 400 ppm NO+100 ppm $NO_2$ in 3% $O_2$ at 500° C. It is clear that in the presence of $NO_2$, the signal for NO is considerably diminished, indicating significant interference.

Using a Type 1 sensor, as shown in FIG. 1, we measured the NO response in a fixed $O_2$ concentration (5%) at temperatures varying from 500–700° C. This temperature range was chosen because YSZ begins to show significant ionic conduction only above 450° C. and zeolite Y retains a crystalline structure up to 750° C. It was observed that the sensitivity of the sensor decreased with increasing temperature with virtually no sensor response at 700° C. Two possible reasons for the diminished sensor sensitivity are preferential oxidation of NO at the Pt surface rather than at the Pt-YSZ boundary at higher temperatures, and also diminished adsorption of NO at the triple points on the Pt-YSZ at higher temperatures. This temperature dependence is consistent with previous measurements, e.g. on $CdCr_2O_4$ electrodes on YSZ, significant loss of sensitivity at 600° C. was reported.

The automotive sensor probe shown in FIGS. 4 and 5 was tested in an automotive engine set up 170 as shown in FIG.

Figure 18:
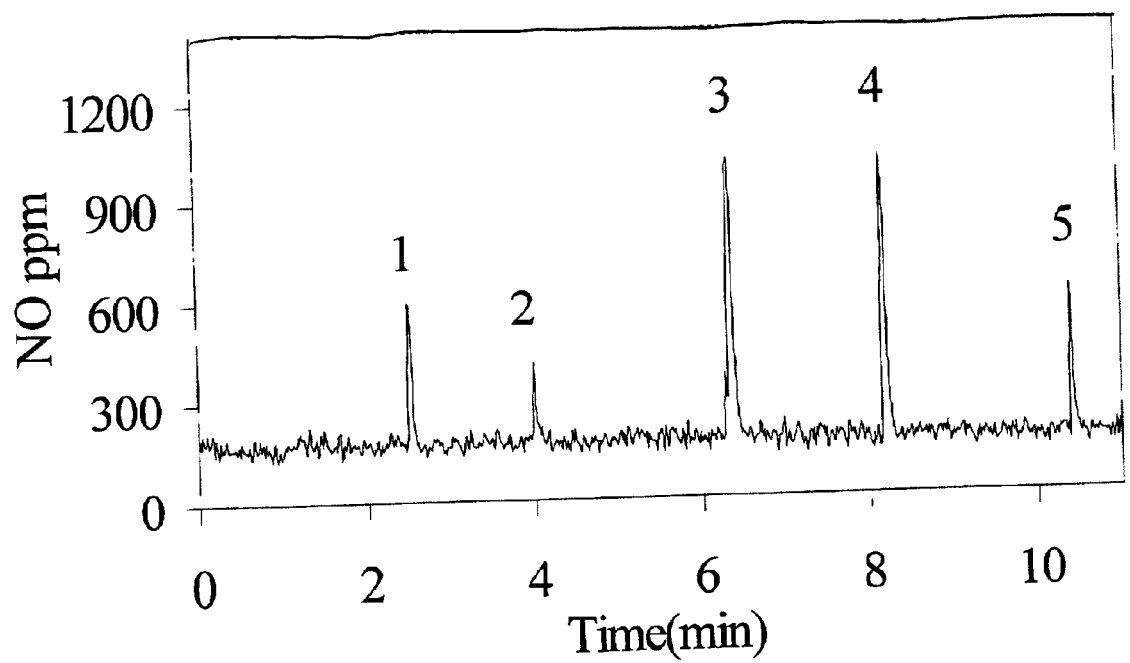
FIG. 18 shows a typical NO emission profile as measured by IR.
Figure 19:
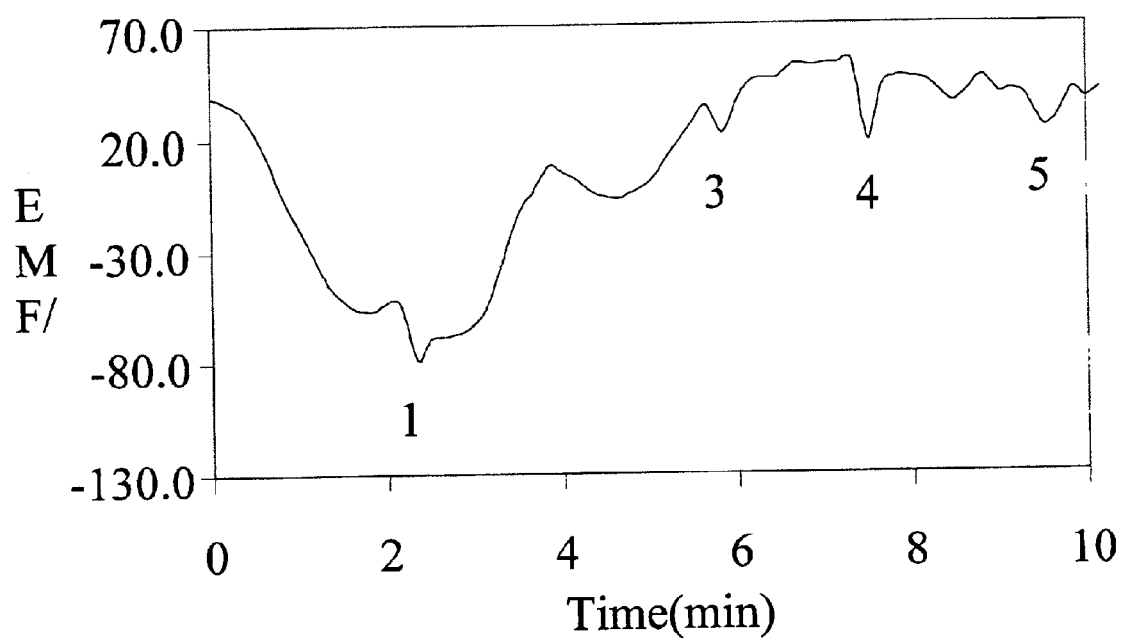
FIG. 19 shows the output of the NO sensor.

17. The automotive engine set up 170 comprises a dyno 171 connected to an engine 174. A sensor 173 is disposed in the exhaust stream of the engine. The gas flow direction is indicated by 177. An online IR analyzer 175 was used to verify the sensor response. The level of NO in the emission was altered by adjusting the engine speed and a typical NO emission profile as measured by the IR is shown in FIG. 18. The output of the NO sensor is plotted in FIG. 19 and the peaks follow a similar time profile as the IR output (see FIG. 18, event 2, where no response of the NO sensor is observed). These preliminary data are encouraging, in that the sensor packaging survived repeated tests. The response time of the sensor is comparable to that of the IR detector. There is a delay in the response of the IR due to the length of the gas transfer line, which accounts for the small absolute time difference in the sensor and IR signals. The temperature of the exhaust stream fluctuated as the engine speed was altered and could be responsible for the changing backgrounds. Heating of the YSZ to minimize the effect of the temperature fluctuations is currently being investigated.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims, which are incorporated herein by reference.

REFERENCES

1. N. Miura, G. Lu and N. Yamazoe, *Sensors and Actuators B*, 52 (1998) 169–178.
2. N. Miura, H. Kurosawa, M. Hasei, G. Lu and N. Yamazoe, *Solid State Ionics*, 86–88 (1996) 1069–1073.
3. N. Miura, G. Lu, N. Yamazoe, H. Kurosawa and M. Hasei, *J. Electrochem. Soc.* 143 (2) (1996) L33–L35.
4. G. Lu, N. Miura and N. Yamazoe, *Sensors and Actuators B*, 65 (2000) 125–127.
5. H. Kurosawa, Y. Yan, N. Miura and N. Yamazoe, *Solid State Ionics*, 79 (1995) 338–343.
6. E. L. Brosha, R. Mukundan, D. R. Brown, F. H. Garzon, J. H. Visser, M. Zanini, Z. Zhou and E. M. Logothetis, *Sensors and Actuators B*, 69 (2000) 171–182.
7. R. Mukundan, E. L. Brosha, D. R. Brown and F. H. Garzon, *Electrochemical and Solid State Letters*, 2(8) (1999) 412–414.
8. R. Mukundan, E. L. Brosha, D. R. Brown and F. H. Garzon, *J. Electrochem. Soc.* 147 (4) (2000) 1583–1588.
9. T. Hibino, S. Kakimoto and M. Sano, *J. Electrochem. Soc.* 146 (9) (1999) 3361–3366.
10. A. Walcarius, "Zeolite-Modified Electrodes in Electroanalytical Chemistry", *Analytical Chimica Acta*, 384, pp. 1–16 (1999).
11. A. Walcarius, "Factors Affecting the Analytical Applications of Zeolite Modified Electrodes: Indirect Detection of Nonelectroactive Cations", *Analytical Chimica Acta*, 388, pp. 79–91 (1999).
12. K. Fukui, S. Nishida, "CO Gas Sensor Based on Au—$La_2O_3$ Added $SnO_2$ Ceramics with Siliceous Zeolite Coat", *Sensors and Actuators B*, 45, pp. 101–106 (1997).
13. H. Tsuchiya, I. Sasaki, A. Harano, T. Okubo and M. Sadakata, "Zeolite Sensor for Nitrogen Monoxide Detection at High Temperature", *Mat. Res. Soc. Symp. Proc.*, 454, pp. 297–302 (1997).
14. O. Enea, "Morphological and Electrocatalytic Properties of Gold Deposits on NaY Zeolite", *Electrochim. Acta.*, pp. 1647 34 (1989).
15. M. Osada, I. Sasaki, M. Nishioka, M. Sadakata, T. Okubo, "Synthesis of a Faujasite Thin Layer and its Application for $SO_2$ Sensing at Elevated Temperatures", *Microporous and Mesoporous Materials*, 23, pp. 287–294 (1998).
16. B. Liu, F. Yang, J. Kong, J. Deng, "A Reagentless Amperometric Biosensor Based on the Coimmobilization of Horseradish Peroidase and Methylene Green in a Modified Zeolite Matrix", *Analytica Chimica Acta*, 386, pp. 31–39 (1999).
17. U. Kunzellman, H. Bottche, "Biosensor Properties of Glucose Oxidase Immobilized Within $SiO_2$ Gels", *Sensors and Actuators B*, 39, pp. 222–228 (1997).
18. U. Simon, U. Flesch, W. Maunz, R. Muller, C. Plog, "The effect of $NH_3$ on the Ionic Conductivity of Dehydrated Zeolites Nabeta and Hbeta", *Microporous and Mesoporous Materials*, 21, pp. 111–116 (1998).
19. O. S. Wolfbeis, "Novel Oxygen Sensor Material Based on a Ruthenium Bipyridyl Complex Encapsulated in Zeolite Y: Dramatic Differences in the Efficiency of Luminescence Quenching by Oxygen on Going From Surface-Absorbed to Zeolite-Encapsulated Flourophores", *Sensors and Actuators B*, 29, pp. 240–245 (1995).
20. R. Berger, Ch. Gerber, H. P. Lang, J. K. Gimzewski, "Micromechanic: A Toolbox for Femtoscale Science: Towards a Laboratory on a Tip", *Microelectronic Engineering*, 35, pp. 373–379 (1997).
21. L. Scandella, G. Binder, T. Mezzacasa, J. Gobrecht, R. Berger, H. P. Lang, Ch. Gerber, J. K. Gimzewski, J. H. Koegler, J. C. Jansen, "Combination of Single Crystal Zeolites and Microfabrication: Two Applications Toward Zeolite Nanodevices", *Microporous and Mesoporous Materials*, 21, pp. 403–409 (1998).

The aforementioned references are hereby incorporated herein by reference.

What is claimed is:

1. A $NO_X$ potentiometric sensor for determining the concentration of $NO_X$ in a gas stream comprising:
    a tube, said tube having an end, an interior and an exterior;
    a cap member comprising yttria-stabilized zirconia disposed on said end of said tube so as to close said end of said tube, said cap member having an interior surface exposed to the interior of said tube and an exterior surface;
    a first electrode disposed on said interior surface of said cap member;
    a second electrode disposed on said exterior surface of said cap member; and
    a zeolite coating disposed on said first electrode, said zeolite coating capable of oxidizing NO in said gas stream to $NO_2$ such that said first electrode is exposed to a higher concentration of $NO_2$ than said second electrode.

2. The $NO_X$ potentiometric sensor according to claim 1 additionally comprising a potentiometer, said potentiometer in electrical communication with said first electrode and said second electrode so as to measure a potential difference between said first electrode and said second electrode.

3. The $NO_X$ potentiometric sensor according to claim 1 wherein said tube comprises alumina.

4. The $NO_X$ potentiometric sensor according to claim 1 wherein said first electrode comprises a material selected from the group consisting of platinum, gold and $Cr_2O_3$.

5. The $NO_X$ potentiometric sensor according to claim 1 wherein said second electrode comprises a material selected from the group consisting of platinum, gold and $Cr_2O_3$.

6. The NO$_X$ potentiometric sensor according to claim 1 wherein said zeolite is zeolite Y.

7. A NO$_X$ potentiometric sensor for determining the concentration of NO$_X$ in a gas stream comprising:
- a tube comprising yttria-stabilized zirconia, said tube having an exterior surface and an interior surface;
- a first electrode disposed on said exterior surface of said tube;
- a second electrode disposed on said interior surface of said tube; and
- a zeolite covering said first electrode, said zeolite coating capable of oxidizing NO in said gas stream to NO$_2$ such that said first electrode is exposed to a higher concentration of NO$_2$ than said second electrode.

8. The NO$_X$ potentiometric sensor according to claim 7 additionally comprising a potentiometer, said potentiometer in electrical communication with said first electrode and said second electrode so as to measure a potential difference between said first electrode and said second electrode.

9. The NO$_X$ potentiometric sensor according to claim 7 wherein said first electrode comprises a material selected from the group consisting of platinum, gold and Cr$_2$O$_3$.

10. The NO$_X$ potentiometric sensor according to claim 7 wherein said second electrode comprises a material selected from the group consisting of platinum, gold and Cr$_2$O$_3$.

11. The NO$_X$ potentiometric sensor according to claim 7 wherein said zeolite is zeolite Y.

12. The NO$_X$ potentiometric sensor for determining the concentration of NO$_X$ in a gas stream comprising:
- a substrate comprising yttria-stabilized zirconia;
- a first electrode disposed on said substrate;
- a second electrode disposed on said substrate; and
- a zeolite coating disposed on said second electrode, said zeolite coating capable of oxidizing NO in said gas stream to NO$_2$ such that said second electrode is exposed to a higher concentration of NO$_2$ than said first electrode.

13. The NO$_X$ potentiometric sensor according to claim 12 additionally comprising a potentiometer, said potentiometer in electrical communication with said first electrode and said second electrode so as to measure a potential difference between said first electrode and said second electrode.

14. The NO$_X$ potentiometric sensor according claim 12 wherein said first electrode comprises a material selected from the group consisting of platinum, gold and Cr$_2$O$_3$.

15. The NO$_X$ potentiometric sensor according claim 12 wherein said second electrode comprises a material selected from the group consisting of platinum, gold and Cr$_2$O$_3$.

16. The NO$_X$ potentiometric sensor according claim 12 wherein said zeolite is zeolite Y.

17. The NO$_X$ potentiometric sensor according to claim 12 wherein said substrate, said first electrode and said second electrode are shielded from direct contact by an exhaust gas by a porous member that permits said exhaust gas to travel through said porous member such that said exhaust gas indirectly contacts said first and said second electrodes, said porous member additionally protecting said substrate, said first and said second electrodes from degradation caused by said exhaust gas.

18. A NO$_X$ potentiometric sensor for determining the concentration of NO$_X$ in a gas stream comprising:
- a yttria-stabilized zirconia substrate;
- a first electrode disposed on said yttria-stabilized zirconia substrate;
- a second electrode disposed on said yttria-stabilized zirconia substrate;
- a zeolite coating disposed on said first electrode, said zeolite coating capable of oxidizing NO in said gas stream to NO$_2$ such that said first electrode is exposed to a higher concentration of NO$_2$ than said second electrode.

19. The NO$_X$ potentiometric sensor according to claim 18 wherein said first electrode comprises a material selected from the group consisting of platinum, gold, and Cr$_2$O$_3$.

20. The NO$_X$ potentiometric sensor according to claim 18 wherein said second electrode comprises a material selected from the group consisting of platinum, gold, and Cr$_2$O$_3$.

21. The NO$_X$ potentiometric sensor according to claim 18 wherein said first electrode and said second electrode are constructed from the same material.

22. The NO$_X$ potentiometric sensor according to claim 18 wherein said zeolite is zeolite Y.

* * * * *

UNITED STATES PATENT AND TRADEMARK OFFICE
CERTIFICATE OF CORRECTION

PATENT NO.   : 6,843,900 B2
DATED        : January 18, 2005
INVENTOR(S)  : Dutta et al.

It is certified that error appears in the above-identified patent and that said Letters Patent is hereby corrected as shown below:

Title page,
Item [56], References Cited, OTHER PUBLICATIONS, insert

-- Zhuiykov, S. et al., *Stabilized Zirconia-Based NOx Sensor Using ZnFe2O4 Sensing Electrode*, Electrochemical and Solid-State Letters, 4 (9), H19-H21 (2001).

Ruhland, B. et al., *Gas-kinetic Interactions of Nitrous Oxides with SnO2 Surfaces*, Sensors and Actuators B 50, 85-94 (1998).

Imanaka, N. et al., *Nitrogen Oxides Sensor Based on Silicon Nitride Refractory Ceramics*, Electrochemical and Solid-State Letters, 2 (2), 100-101 (1999).

Zhuiykov, S. et al., *Potentiometric NOx Sensor Based on Stabilized Zirconia and NiCr2O4 Sensing Electrode Operating High Temperatures*, Electrochemistry Communications 3, 97-101 (2001).

Miura, N. et al., *Selective Detection of NO by Using an Amperometric Sensor Based on Stabilized Zirconia and Oxide Electrode*, Solid State Ionics 117, 283-290 (1999).

Sberveglieri, G., et al., *Response to Nitric Oxide of Thin and Thick SnO2 Films Containing Trivalent Additives*, Sensors and Actuators B1, 79-82 (1990).

Baratto, C. et al., *Gold-Catalysed Porous Silicon for NOx Sensing*, Sensors and Actuators B 68, 74-80 (2000).

Fruhberger, B. et al:, *Detection and Quantification of Nitric Oxide in Human Breath Using a Semiconducting Oxide Based Chemiresistive Microsensor*, Sensors and Actuators B 76, 226-234 (2001).

Ono, M. et al., *Amperometric Based on NASICON and NO Oxidation Catalysts for Detection of Total NOx in Atmospheric Environment*, Solid State Ionics 136-137, 583-588 (2000).

Fleischer, M. et al., *Selective Gas Detection with High-Temperature Operated Metal Oxides Using Catalytic Filters*, Sensors and Actuators B 69, 205-210 (2000).

Kitsukawa, S. et al., *The Interference Elimination for Gas Sensor by Catalyst Filters*, Sensors and Actuators B 65, 120-121 (2000).

UNITED STATES PATENT AND TRADEMARK OFFICE
CERTIFICATE OF CORRECTION

PATENT NO. : 6,843,900 B2
DATED : January 18, 2005
INVENTOR(S) : Dutta et al.

It is certified that error appears in the above-identified patent and that said Letters Patent is hereby corrected as shown below:

Title page (cont'd),

Hugon, O. et al., *Gas Separation with a Zeolite Filter, Application to the Selectivity Enhancement of Chemical Sensors*, Sensors and Actuators B 67, 235-243 (2000).
Kaneyasu, K. et al., *A Carbon Dioxide Gas Sensor Based on Solid Electrolyte for Air Quality Control*, Sensors and Actuators B66, 56-58 (2000).

Szabo, N. et al., *Microporous Zeolite Modified yttria Stabilized Zirconia (YSZ) Sensors for Nitric Oxide (NO) Determination in Harsh Environments*, Sensors and Actuators B 4142, 1-8 (2001). --

Signed and Sealed this

Twenty-third Day of May, 2006

JON W. DUDAS
*Director of the United States Patent and Trademark Office*